United States Patent [19]
Suzuki et al.

[11] Patent Number: 5,368,047
[45] Date of Patent: Nov. 29, 1994

[54] SUCTION-TYPE BLOOD SAMPLER

[75] Inventors: Yoshihiko Suzuki, Honmachi; Kazunori Murakami, Otsu, both of Japan

[73] Assignee: Nissho Corporation, Osaka, Japan

[21] Appl. No.: 215,706

[22] Filed: Mar. 22, 1994

[30] Foreign Application Priority Data

Apr. 28, 1993 [JP] Japan .................. 5-125013

[51] Int. Cl.⁵ .............................................. A61B 17/34
[52] U.S. Cl. ..................... 128/765; 128/763; 128/770; 606/182; 606/181
[58] Field of Search ............... 128/749, 751, 752, 753, 128/754, 757, 758, 761, 763, 764, 765, 770; 606/181, 182

[56] References Cited

U.S. PATENT DOCUMENTS

| | | | |
|---|---|---|---|
| 3,208,452 | 9/1965 | Stern | 606/182 |
| 4,203,446 | 5/1980 | Hofert et al. | 606/182 |
| 4,379,456 | 4/1983 | Cornell et al. | 128/314 |
| 4,449,529 | 5/1984 | Burns et al. | 606/182 |
| 4,462,405 | 7/1984 | Ehrlich | 128/329 |
| 4,653,513 | 3/1987 | Dombrowski | 128/765 |
| 5,029,583 | 7/1991 | Meserol et al. | 128/763 X |
| 5,188,118 | 2/1993 | Terwilliger | 128/753 |

FOREIGN PATENT DOCUMENTS 1551362  3/1990  U.S.S.R. ................. 128/754

*Primary Examiner*—Sam Rimell
*Attorney, Agent, or Firm*—Adduci, Mastriani, Schaumberg & Schill

[57] ABSTRACT

A blood sampler of the suction-type is provided with a gasket, a lancet unit and a plunger slidable in a housing having an open front and an open rear end. A rod is connected at its front end to the lancet unit. The rod extends rearwardly over a detent integral with the inner periphery of the housing, through a central opening of the gasket and into an axial bore of the plunger. A flange, secured to the rear end of the rod is slidable within the axial bore, the gasket is slidable within the housing and behind the detent, and a protrusion formed integral with an intermediate portion of the rod is engageable with the detent. The blood sampler further has a first spring intervening between the detent and the lancet unit, and a second spring accommodated in the bore and intervening between the flange and the front end of the plunger.

15 Claims, 8 Drawing Sheets

Fig.8
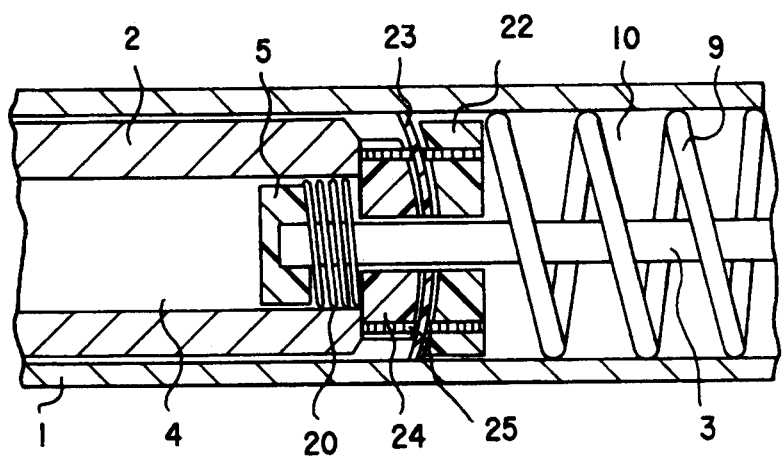
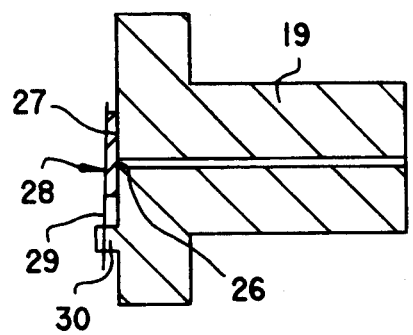
Fig.10
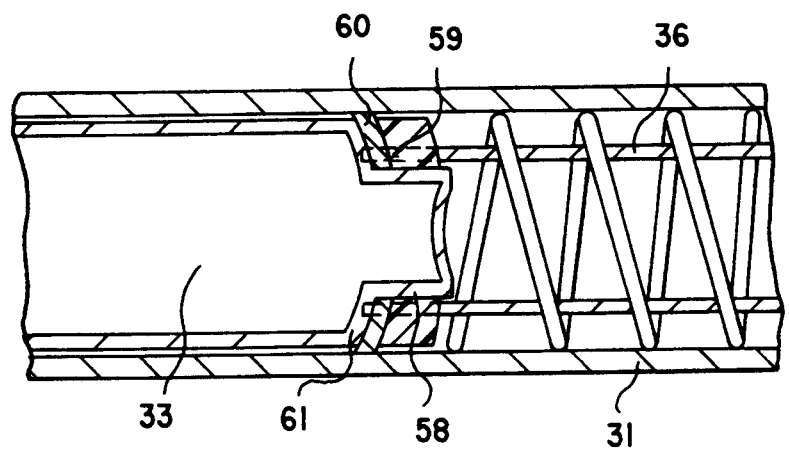
Fig.18

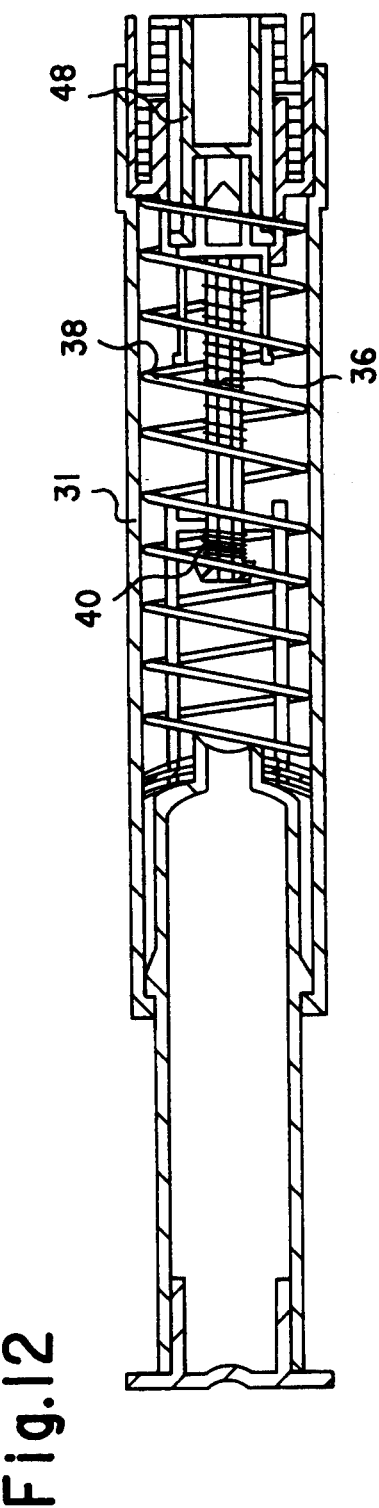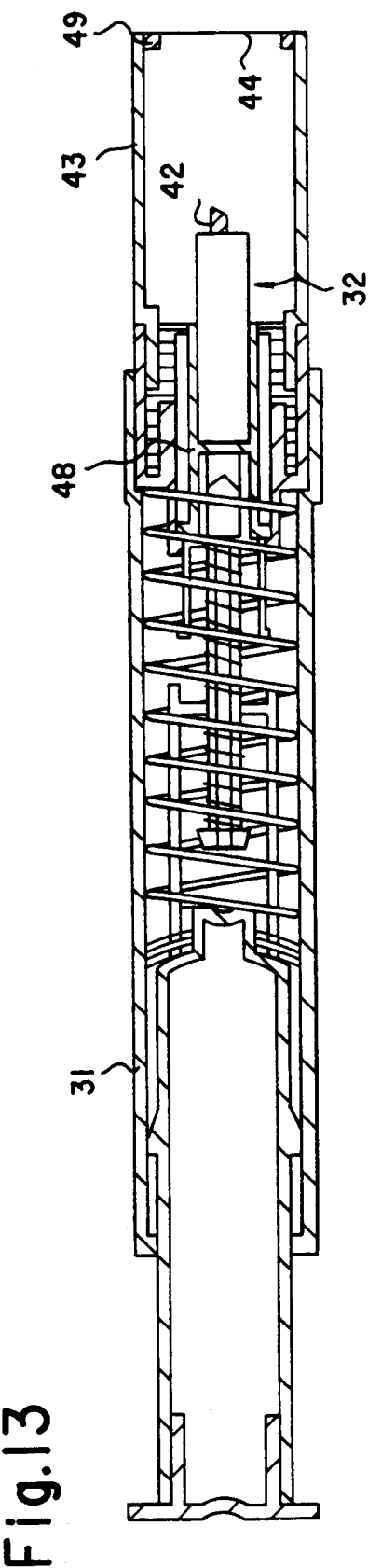

SUCTION-TYPE BLOOD SAMPLER

BACKGROUND OF THE INVENTION

1. Field of the Invention

The present invention relates to a blood sampler of the suction type useful for sampling from a human skin a predetermined quantity of blood for various blood tests, by thrusting a sting or needle into the human skin, wherein a vacuum of a certain degree is applied thereto to suck the blood sample into the device.

2. Description of Prior Art

Generally, so-called lancet injectors comprise a blade and a pressable end opposed thereto, with the blade having an acute end capable of being thrust into the skin of a human. By gently striking the pressable portion, the acute end of the blade will pierce the skin, for example, that of his or her finger. A small amount of blood for the blood test will ooze out of the skin, and will be taken into a container by using a pipette or capillary. There are many small blood vessels in each finger so that a finger can be pressed to cause a small drop of blood to ooze. Since fingers are more sensitive to pain, it is a recent tendency that the upper arm, abdomen or thigh is subjected to the blood sampling. Similar devices are also used in the latter case too, and an example thereof is disclosed in the U.S. Pat. No. 4,653,513. This device comprises a cylindrical housing and a lancet support, which has a gasket or flexible portion slidably accommodated in the housing. Springs will retract the lancet support to thereby reduce air pressure in the housing so that it sucks a blood sample, automatically and immediately after a lancet pierces the skin.

The gasket in the prior art device is however rigidly secured to the lancet support. The gasket is in air-tight contact with the inner peripheral surface of the housing. Friction between the gasket and said surface will lower the thrust speed of the lancet or needle, thereby increasing pain when the lancet pierces the skin. Further, the lancet support is automatically locked at its position where the skin continues to stick to the device, due to the reduced air pressure. If the cylindrical housing is forced off the skin, then it will spring back and ambient air rushes into the housing. In such an event, blood will scatter or otherwise discharge out of the device, and consequently a somewhat superfluous amount of blood has to be taken.

SUMMARY OF THE INVENTION

An object of the present invention is therefore to provide a blood sampler of the suction or vacuum type that can pierce human skin at a high speed when drawing a sample of a desired quantity of blood, and prevent the collected blood from scattering.

A blood sampler of the suction type provided herein comprises: a housing; a lancet unit accommodated in a front region of the housing; a rod extending rearwardly from the lancet unit; a plunger accommodated in a rear region of the housing and having a gasket attached to a forward end of the plunger; the rod connected to the plunger; and, the housing having an open frontal end and an open rearward end. The lancet unit has a lancet body fixed to a lancet retainer with a needle extending forwardly therefrom. The lancet retainer is in sliding contact with the inner periphery of the housing. Accommodated in the housing and between the lancet unit and the plunger are a first spring, a second spring and a third spring. The first spring urges the lancet unit forward to cause the needle to jut or extend from the frontal end of the housing. The second spring urges the lancet unit to be retracted behind the frontal end while the plunger is being temporarily pressed. The third spring subsequently acts to reduce the air pressure in the housing, when the plunger is unpressed to be free.

In operation of a preferred embodiment (shown in FIG. 1), the plunger will be retracted at first to slide on and along the inner periphery of the housing, until a protrusion on the rod engages with a concave detent formed on the inner periphery of the housing. The lancet unit takes its stationary position within the housing in this manner, and the first spring becomes compressed. Then, the open frontal end of the housing will be pressed to the skin of a human. Subsequently, the plunger will be forced forward to disengage the protrusion from the detent to thereby permit the compressed first spring to stretch itself. As a result, the needle will spring out ahead the frontal end of the housing so as to penetrate the skin. At the same time as the movement of these members, a flange fixed to the rod and held in an axial chamber of the plunger will also move forward. This movement of the flange will compress the second spring that has been in its stretched or uncompressed state. Thus, a resilient recoiling of the second spring that tends to stretch again will kick the plunger backward immediately after the needle's penetration. Due to the backward movement of the plunger, the needle will be return to its home position in the housing. The thus freed third spring which has been compressed can now stretch itself, which in turn will force the plunger to slide further backward within the housing. The gasket carried by the plunger will also make a backward sliding movement in harmony with the plunger and in contact with the housing's inner periphery. In this manner, the internal air pressure of the housing will be reduced between the gasket and the housing's frontal end which is in contact with the skin. Such a reduced internal pressure will draw or suck a necessary quantity of sample blood into the device, through the needle penetrating the skin. By inspecting this process through a transparent front wall of the housing, the plunger will be pressed forward a little when the collecting of the required quantity of blood is completed. This forward pressing of the plunger will produce a clearance between the gasket's periphery and the inner periphery of the housing. Ambient air enters the housing through the clearance to thereby recover atmospheric pressure in the housing and to stop the drawing or sucking of the sample blood. Vacuum attraction of the skin portion will also cease, and the skin will recover its natural state.

In another embodiment (shown in FIG. 11) of the present invention, the suction-type blood sampler will operate as follows. Similarly to the embodiment already described above, the open frontal end of the housing will be pressed to human skin. Subsequently, the plunger will be forced forward to cause an inner cylindrical member to move forward, until its frontal end simultaneously contacts a hookable member and compresses the first spring. By further pressing the plunger, a rear edge of the hookable member will advance beyond a rear inner flange of a front cylindrical cap. The rear edge will thus engage with and stop in the cylindrical cap, and the first spring that has been compressed will be released. As a result, the needle held by the lancet body will spring out ahead of the frontal end of the housing so as to penetrate the skin. At the same time as these motions of the members, as the hookable member slides forward within and forwardly of the housing, the second spring that has been stretched will start to be compressed so that a resilient recoil thereof urges the lancet unit backward to return the needle to its home position in the front cap. Next, the plunger that has been pressed forward by a user will be released so that the third spring that has been in its compressed state can be released. Thus, the plunger will move backward and the internal air pressure of the housing will be reduced in the region between the frontal end in contact with the skin and the gasket. Such a reduced internal pressure will draw or suck a quantity of sample blood into the device. By inspecting this process through a transparent front wall of the housing, the plunger will be pressed slightly forward when the required quantity of blood has been taken. This forward pressing of the plunger will produce a clearance between the gasket's periphery and the inner periphery of the housing. Ambient air would enter the housing through the clearance to thereby recover atmospheric pressure in the housing.

BRIEF DESCRIPTION OF THE DRAWINGS

FIGS. 2 to 7 illustrate in a step by step manner an operation of the blood sampler in FIG. 1, sequentially from an initial step to a final step of the operation, in which:

FIG. 2 is a cross-section showing a lancet retainer protruding forwardly of a housing of the blood sampler;

FIG. 3 similarly shows a lancet unit comprising the lancet retainer, with the unit being set in its ready state by pulling back a plunger of the blood sampler;

FIG. 4 also shows the plunger which has been pressed forward to compress a third spring;

FIG. 5 shows the lancet unit driven forward by a first spring so that a forward end of a needle fixed in the lancet retainer protrudes outwardly of the housing;

FIG. 6 similarly shows the lancet unit retracted by a second spring which has stretched itself in a recoiling manner; and FIG. 7 finally shows the plunger retracted to its home position by the third spring;

FIG. 8 is an enlarged cross-section of a gasket and relevant members adjacent thereto and employed in the blood sampler in the embodiment shown in FIG. 1;

FIG. 10 shows an example of a ventilation bore formed through a plug fitted in the plunger;

FIGS. 12 to 17 sequentially illustrate an operation of the blood sampler shown in FIG. 11, in a manner corresponding to FIGS. 2 to 7 for the first mentioned embodiment, respectively; and FIG. 18 is an enlarged cross-section of a gasket and relevant members adjacent thereto and employed in the blood sampler in the embodiment shown in FIG. 11.

DETAILED DESCRIPTION OF THE PREFERRED EMBODIMENTS

Figure 1:
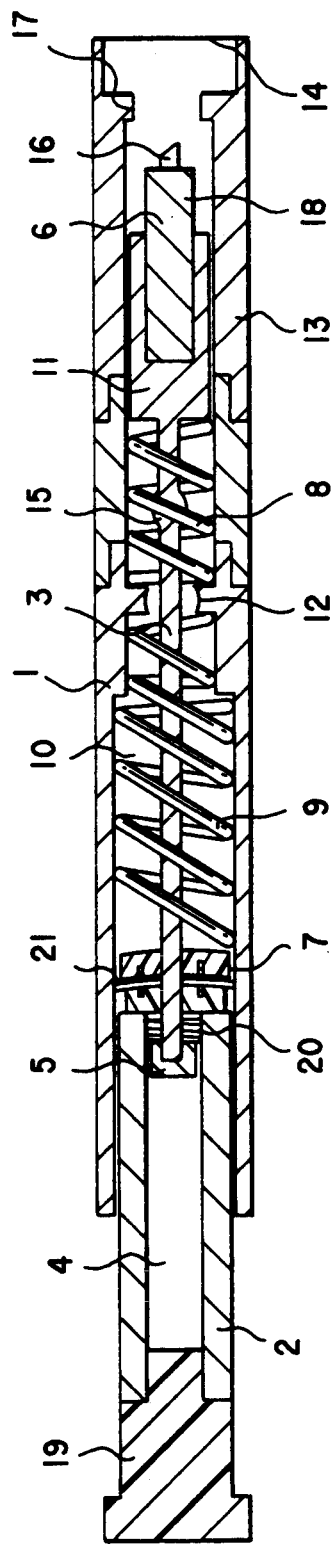
FIG. 1 is a cross-section of a suction-type blood sampler in an embodiment of the invention.

A suction-type blood sampler provided according to an embodiment shown in FIG. 1 comprises a cylindrical cap 13 fitted on a frontal end of a housing 1. A lancet unit 6 held by a lancet retainer 11 has a needle 16 in a position prior to piercing the skin. The lancet unit 6 consists of a needle 16 and a lancet body 18 carrying the needle. Although the housing 1 is open at both ends, the cap 13 extending from the frontal end and surrounding the lancet unit 6 will protect a user or patient from being injured by the needle when the needle is in a retracted state. The frontal cap 13 may be transparent so that the user can accurately complete the sampling of a required quantity of blood. The lancet body 18 holding the needle 16 may be replaced with a new body prior to the next use. An annular lug or rim 17 protrudes radially inward from a portion of the cap 13, with the portion being located 1 mm or more behind the frontal end 14 of the cap. The rim 17 will engage with and stop the front end of the lancet retainer 11, so that the needle 16 is prevented from springing an excessive distance beyond the forward end 14. Thus, the depth to which the needle pierces the skin is regulated by the rim.

A rod 3 in the housing 1 extends rearwardly from the lancet unit 6 and beyond a concave detent 12 which protrudes from the inner periphery of the housing. The rod 3 further extends through a central opening 21 of a gasket 7 into an axial bore 4 formed in a plunger. A flange 5 fixed to the rear end of the rod 3 is slidable in the axial bore 4. A second spring 20 disposed in the axial bore 4 intervenes between an entrance thereof and the flange 5. The plunger 2 is movable forwardly to disengage a protrusion 15 formed on the rod 3 from the concave detent 12. The second spring 20 will act to retract the needle 16 back into the housing, immediately after the needle passes through the open end 14 and pierces the skin. The flange 5 may be made of rubber or elastic material, or any appropriate plastic.

The protrusion 15 integral with the rod 3 extends to interfere with an inner circular face of the detent 12 of the housing 1. If the protrusion is engaged with the detent, then the lancet unit 6 can not move further forward to extend or jut through the open end 14. The plunger 2, slidable in the rear region of the housing, is disposed behind the concave detent 12. The gasket 7 attached to the front surface of the plunger provides an air-tight and slidable engagement thereof with the housing's inner periphery. The central opening 21 formed axially through the gasket 7 allows the rod 3 to extend across the interior 10 into the axial bore 4 of the plunger. The gasket, which may be made of rubber, is in air-tight contact with the inner periphery of the housing. A plug 19, closing a rear open end of the axial bore 4, may also be made of an appropriate rubber.

It is important that the gasket 7 ensures a reduced friction contact between the inner periphery of the housing 1 and the plunger 2 moving therein fore and aft. Further, the gasket 7 preferably permits the air in the housing interior 10 to escape backward when the plunger moves forward. On the other hand, the gasket must allow adiabatic expansion of the internal air so as to enhance an improved vacuum sucking ability to the blood sampler when the plunger moves backward. To meet these requirements, a clearance is provided between the periphery of the gasket 7 and the inner periphery of the housing 1, for free forward movement of the plunger 2. The gasket's periphery is kept in airtight contact with the housing's periphery while the plunger is moving backward.

FIG. 8 is a cross-section of an example of the gasket 7 used herein. This gasket, made of the rubber or the like, includes a front disc 22, a rear disc 24 having a smaller diameter than the front disc, and a flexible sheet 23 sandwiched between the discs. The flexible sheet is curved backward toward the plunger and has a periphery in contact with the housing's inner periphery. A gap or clearance will appear between the flexible sheet 23 and the inner periphery, when the plunger moves forward. This gap is effective not only to purge the air from the interior 10 during the forward movement of the plunger 2, but also to introduce ambient air to compensate for a possible evacuation of the interior after the blood sampling. When the plunger 2 moves backward, the flexible sheet 23 will continue to be in an airtight and sliding contact with the inner periphery of the housing 1, thereby lowering the internal pressure below atmospheric pressure. Screws 25 fasten the front and rear discs 22 and 24 and the sheet 23 sandwiched between them to the plunger 2, thus forming the gasket 7. The flexible sheet may desirably be 0.1–5 mm thick, or more preferably 0.5–2 mm thick, and may not necessarily be curved in the described manner but can be formed flat.

Figure 2:
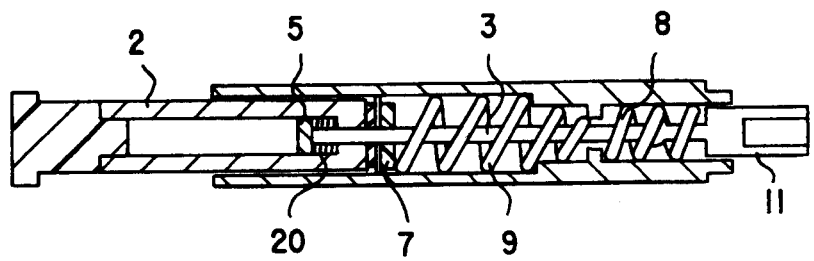

The operation of the suction-type blood sampler is shown sequentially in FIGS. 2 to 7, in this order. In the state shown in FIG. 2, the lancet retainer 11 is exposed out of the front end of the housing 1, due to the first spring 8 that has stretched or expanded itself. The third spring 9 also is in its stretched or expanded state. The lancet body 18 of unit 6 will be attached to the retainer 11 of the blood sampler in this state, before fitting the cylindrical cap 13 on the front end of the housing 1. FIG. 1 shows the needle 16 that is accommodated in the housing in this manner. FIGS. 1 and 2 illustrate a case wherein the lancet body 18 is changed before use of this blood sampler. However, if the sampler is discarded as a whole after use, then the cap 13 may be formed integral with the housing. The annular lug or rim 17 in this case extends radially inwardly from a portion of the housing 1, with the portion also being located 1 mm or more behind the forward end of the elongate housing.

Figure 3:
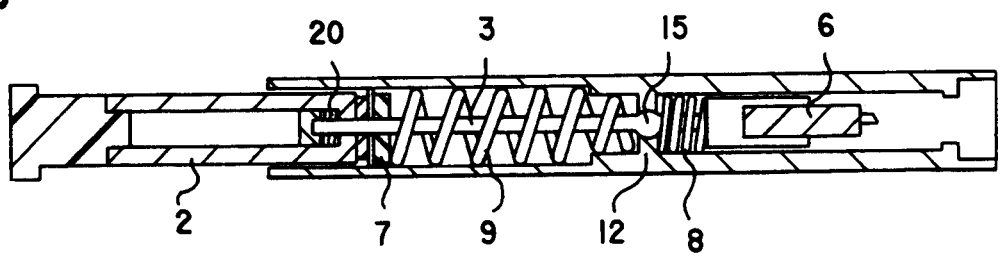

In the next state shown in FIG. 3, the plunger 2 is in its retracted position. The protrusion 15 on the retracted rod 3 is in engagement with the concave detent 12 to keep the lancet unit 6 in place. The third spring 9 remains stretched, with the first spring 8 being compressed. The open end 14 of housing 1 will then be pressed the skin while the blood sampler is either in the state shown in FIG. 2, or in FIG. 3. A strong pressure applied to a portion of the skin by the open end 14 will divert the user's mind from pain, which he or she will feel when his or her skin portion is pierced by the needle. The plunger 2 will subsequently be pressed forward, with the lancet unit 6 remaining in the housing 1. This operation will compress the third spring 9 and thereby cause the flange 5 to move rearward relative to the gasket's central opening 21, within the axial bore 4. At the same time, the compressed second spring 20 stretches itself, in a manner shown in FIG. 4.

Figure 4:
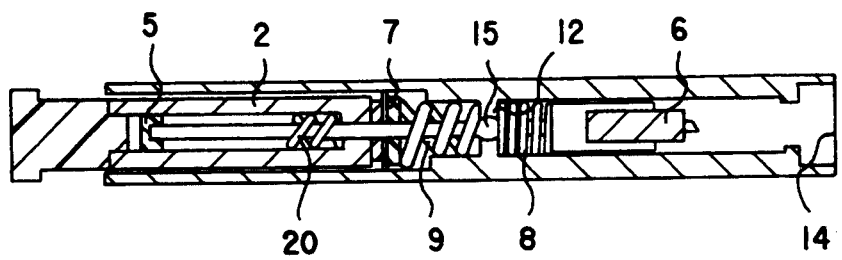
Figure 5:
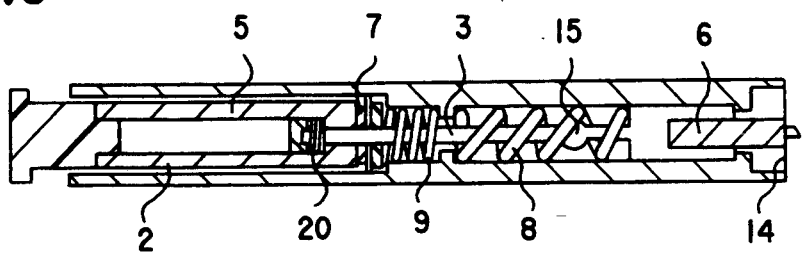
Figure 6:
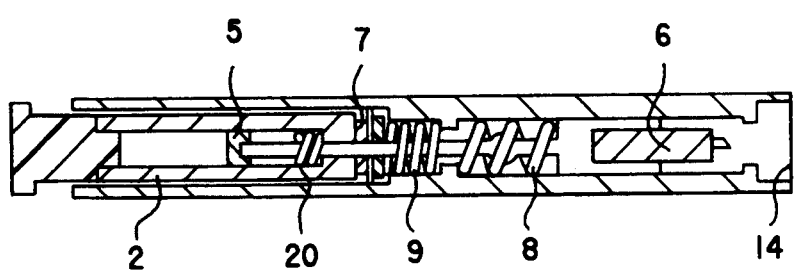

The plunger 2 will be pressed further forward at the next step, wherein the repelling force of the compressed third spring 9 will be overcome as shown in FIG. 4. Such a forcible pressing of the plunger will disengage the protrusion 15 from the detent 12, thus the compressed first spring 8 is released to its stretched or expanded position allowing the lancet unit 6 to spring forward. The needle 16 on the unit will thus protrude from the open end 14 to instantaneously penetrate the human skin, as will be seen in FIG. 5. Simultaneously with those movements of the members, the rod 3 pulls the flange 5 forward within the plunger's axial bore 4 and compresses the second spring 20. The thus compressed second spring 20 will however recover to its uncompressed position immediately after the needle 16 has penetrated the skin as just mentioned above. Therefore, the rod 3 will be retracted in a recoiling manner to restore the needle into the housing, but the first and third springs 8 and 9 remain stretched and compressed, respectively, as shown in FIG. 6.

Figure 7:
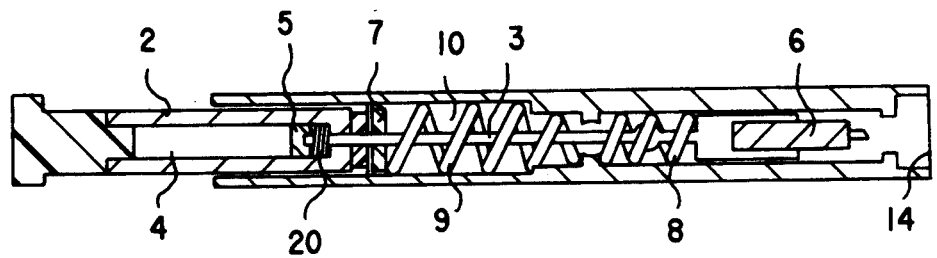

At the following final step, the plunger 2 will be returned to its rearward position before the open end 14 of the housing 1 is removed from the skin. This operation may be done manually, but will however automatically take place due to the action of the compressed third spring 9 which kicks back the plunger as shown in FIG. 6 once the user removes his or her fingers from the plunger. FIG. 7 shows such a final state of the blood sampler. The backward movement of the plunger 2 will reduce air pressure in the interior 10 of the housing. This is because the gasket 7 on the front end of the plunger remains in airtight contact with the inner periphery of the housing and its open end 4 is also in close contact with the skin. Such a reduced air pressure enables the housing to suck a blood sample from the skin portion pierced by the needle. The internal pressure of the housing, which depends on the distance of the backward stroke of the plunger 2, may be 500 mmHg or less preferably 200–300 mmHg, whereas the atmospheric pressure is 760 mmHg. The user can visually check through the transparent cap 13 the blood sample which is being taken, and he or she may adjust the quantity thereof by further actuating the plunger 2 as follows.

The user may press the plunger 2 when the quantity of sample blood has become enough for the blood tests. As the plunger 2 advances forward a little, a gap will appear between the outer periphery of the gasket 7 and the inner periphery of the housing 1. Ambient air will then flow into the housing to recover the atmospheric pressure in the interior 10 so that no further blood is taken. The recovered air pressure will make it possible to remove the open end 14 of the housing 1 away from the skin in which it has been in close contact. This removal of the open end is easy and smooth so that no amount of blood will spill or scatter.

Figure 9:
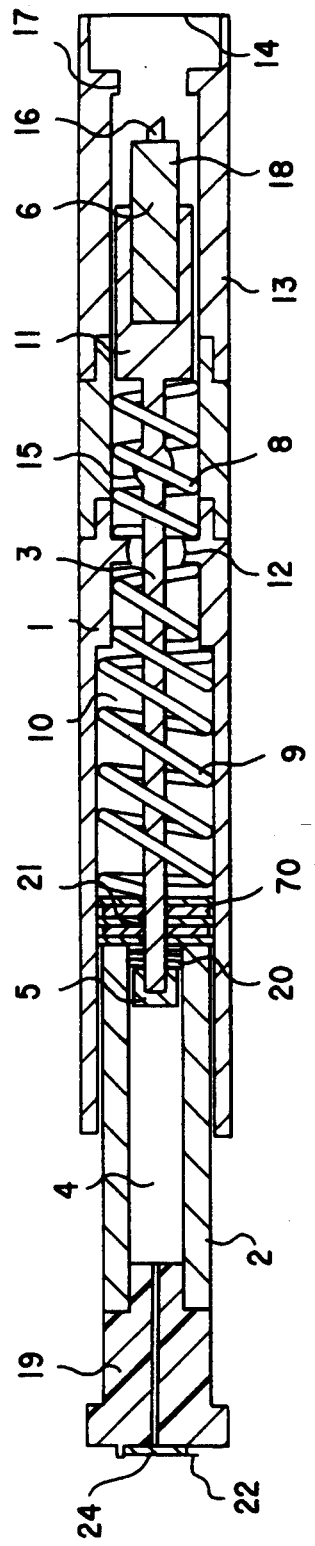
FIG. 9 is a cross-section of the blood sampler provided in a further embodiment.

FIG. 9 shows the blood sampler modified in a further embodiment of the invention. A ventilation bore employed in this case allows ambient air to flow into the housing, if necessary, while the airtight gasket is moving fore and aft within the housing. No amount of air can enter the interior 10 through the contact area from behind the gasket, because a gasket 70 in this case is always in close contact with the housing inner periphery. Therefore, the ventilation bore or aperture 26 is formed in the wall of the housing 1 or plunger 2. Preferably, the bore 26 penetrates the plug 19 so that the air entering the axial bore 4 advances through the central opening 21 and into the interior 10. The ventilation bore 26, which has to be closed during the operation for taking the blood sample, will be opened when the evacuation of interior 10 is to be broken. FIG. 10 shows details of an example of ventilation bore 26 usually closed with an openable lid 28. This lid comprises a plate 29 and an elastic sheet 27 secured thereto, wherein the plate has a basal portion fixed to a lug 30 of the plug 19. The lid 28 will be opened when ambient air is introduced into the plunger's axial bore 4 to raise the reduced air pressure in the housing's interior 10 to atmospheric pressure.

Figure 11:
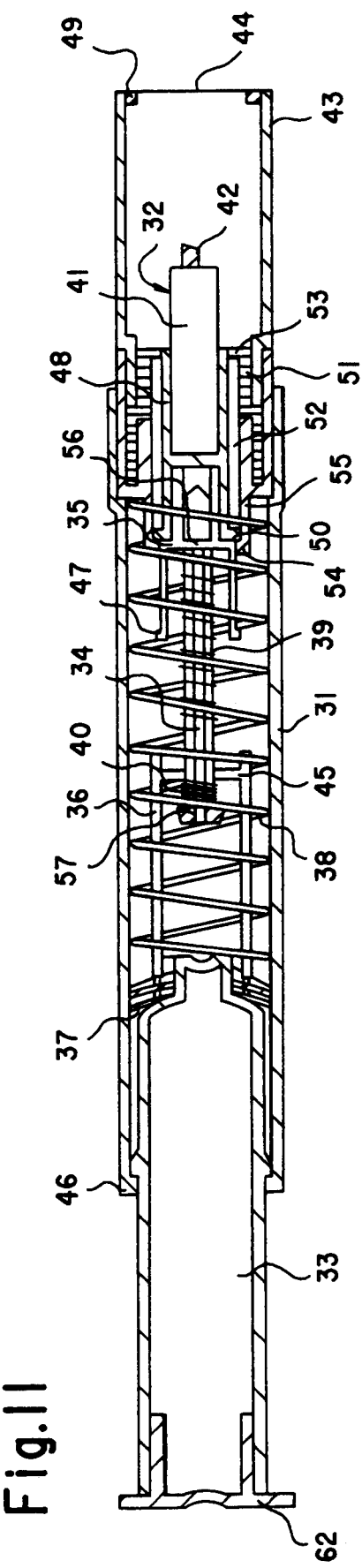
FIGS. 11 is a cross-section of the blood sampler provided in a still further embodiment.

FIG. 11 is a cross-section of a blood sampler provided in a still further embodiment. A cylindrical cap 43 is attached to the front end of a housing 31. A lancet retainer 48 carries a lancet body 41 fitted therein. A needle 42 has not yet been used to pierce the human skin. A lancet unit 32 includes the lancet body 41 carrying the needle and the retainer 48 carrying the body, and a hookable member 35 fits in the lancet retainer 48. An annular lug 50 is formed integral with a rear end of the retainer 48. A first stopper 51 is fixed to the housing 31 to define a front end thereof, and inhibits the retainer 48 from making an excessive advance beyond a predetermined limit of movement. The annular lug 50 moves fore and aft within a cylindrical space 52 formed between a body of the retainer 48 and the stopper 51. The stopper has at its front end a shoulder 53 to limit the advance of the lancet retainer 48. The hookable member 35 has its front portion tightly fitted in a rear cavity of the lancet retainer 48, and has at its rear end an annular or discrete detents 47. A second stopper 55 prevents the lancet retainer from making an excessive rearward movement. The second stopper 55 has a front portion disposed between the first stopper 51 and the front end of the housing 31. A rearward rim or lugs 54 of the second stopper 55 are engageable with the detent or detents 47 of the hookable member 35, but permits it to advance forward beyond the rim or lugs 54.

One of the open ends of the housing 31, that is its front end, continues to the cap 43 covering the needle 42 so as to prevent unintentional injury to the skin. The front cap 43 may preferably be a length of transparent pipe, which enables a user to see if the sucked or drawn amount of sample blood is enough for the blood tests. The lancet body may be replaced with a new body having a new needle. A foremost lug 49 on the inner periphery of the cap will regulate the depth to which the needle penetrates the skin. A rod 34 extends rearwardly from an intermediate bottom 56 of the hookable member 35. An inner cylindrical member 36 has a spring separator 45 integral therewith. The rod 34 which extends through a central opening of the separator is capable of reaching the hookable member's inner and rear region. A second spring 40 loosely fits on the rear portion of the rod having at its rearmost end a flange 57. The flange 57 prevents the rear portion from moving forward through the central opening of the separator 45. A third spring 39 loosely fits on the rod 34, similarly to the second spring 40. The third spring 39 extends from the intermediate bottom 56 of hookable member 35 to the spring separator 45 in the inner cylindrical member 36. The plunger 33, if pressed, will press in turn the third spring 39 and cause the detent 47 of the hookable member 35 to become disengaged from the rearward rim 54 of the second stopper 55 in the front end of the housing 31. Thus, the hookable member 35 advances forward together with the lancet retainer 48 carrying the lancet body 41, until the needle 42 penetrates the skin. On the other hand, the second spring 40, extending from the spring separator 45 of the inner cylindrical member 36 to the flange 57 of the rod 34, is fitted around the rod 34 to retract the needle 42 immediately after it springs out of the open end 44 to penetrate the skin. In detail, the second spring 40 that was compressed until the needle penetrated the skin will be released to expand again, due to its elasticity, to thereby retract the needle back into the cap 43 through the open end 44.

The inner cylindrical member 36 is fixed to and protrudes forwardly from the gasket 37. This member 36 has near its forward end the separator 45 positioned between the third and second springs 39 and 40. The plunger 33 will press the cylindrical member 36 to move forward, until the front end thereof contacts the detent 47 of hookable member 35. The further pressing of the plunger 33 will force the latter member 35 to advance together with the plunger. The plunger 33, slidable on the inner periphery of the housing 31, is inhibited from slipping backwardly off a rearmost lug 46. A front end of the plunger has the gasket 37 in airtight contact with the housing. The gasket is usually made of a rubber or the like elastic material so as to reduce friction between it and the housing. It is also important that the gasket permits the air to escape backward when the plunger moves forward. However, air pressure in the housing must be reduced to such an extent so as to provide the vacuum for drawing a blood sample when the plunger moves backward. To meet this requirement, the gasket periphery has to temporarily form a clearance between it and the housing periphery, during forward movement of the plunger. The gasket however remains in close contact with the inner periphery of housing, during the backward movement of the plunger.

FIG. 18 is a cross-section of an example of the gasket 37 used herein. This gasket comprises a disc 59 made of a rubber or like material and fits on a tip 58 protruding from the plunger 33. An annular flexible sheet 60 is sandwiched between the disc 59 and a front shoulder 61 of the plunger, and is curved backward and has a periphery in contact with the inner periphery of the housing. A clearance will appear between the flexible sheet 60 and the inner periphery when the plunger moves forward. This clearance is effective not only to purge the air from the housing but also to introduce ambient air to compensate for possible evacuation thereof, if necessary, during forward movement of the plunger 33. When the plunger moves backward, the flexible sheet 60 will slide in an airtight manner on the inner periphery, thereby lowering the internal pressure below atmospheric pressure. A rear end of the cylindrical member 36 is threaded to fasten the discs 59 and flexible sheet 60 to the plunger 33, to thereby form the gasket 37. The flexible sheet may be 0.1–5 mm thick, or more preferably 0.5–2 mm thick, and may not necessarily be curved in the described manner but be formed flat.

FIGS. 12 to 17 sequentially show the suction-type blood sampler. In the state shown in FIG. 12, the lancet retainer 48 protrudes forward from the housing 31 and is exposed to the outside, due to the first spring 38 being stretched. The third spring 39 also has stretched itself, with the second spring 40 being compressed. The lancet body 41 of unit 32 will be attached to the retainer 48 in the blood sampler in this state, before fitting the cylindrical cap 43 on the front end of housing 31. FIG. 11 shows the needle 42 accommodated therein in this manner. FIGS. 11 and 12 illustrate the blood sampler wherein the lancet body 41 is changed prior to use of the blood sampler. However, if the sampler is discarded as a whole after use, then the cap 43 may be formed integral with the housing 31. The annular lug or rim 49 in this case may protrude from a portion of the housing 31, also located 1 mm or more behind the forward end 44 thereof.

At the next step shown in FIG. 13, the plunger 33 is driven forward to take its inner position. The first spring 38 and the third spring 9 are compressed to a greater extent, with the second spring 40 further stretched, as compared to their state in FIG. 12. The open end 44 of housing 31 may be pressed against human skin while the blood sampler is either in the state shown in FIG. 12, or in FIG. 13. The open end 44 will be hard pressed to a portion of the skin so that the user's mind may be diverted from the potential pain, which he or she may feel when the portion is pierced by the needle. Subsequently, the plunger 32 will be pressed forward, with the lancet unit 32 not protruding from the housing 31. The third spring 39, thus compressed, will cause the front end of the cylindrical member 36 to bear against the detent 47 located at the rear end of the hookable member 35. At the same time, the third spring 39 is compressed further, as compared with FIG. 13, with the second spring 40 is further stretched in the manner shown in FIG. 14.

Figure 14:
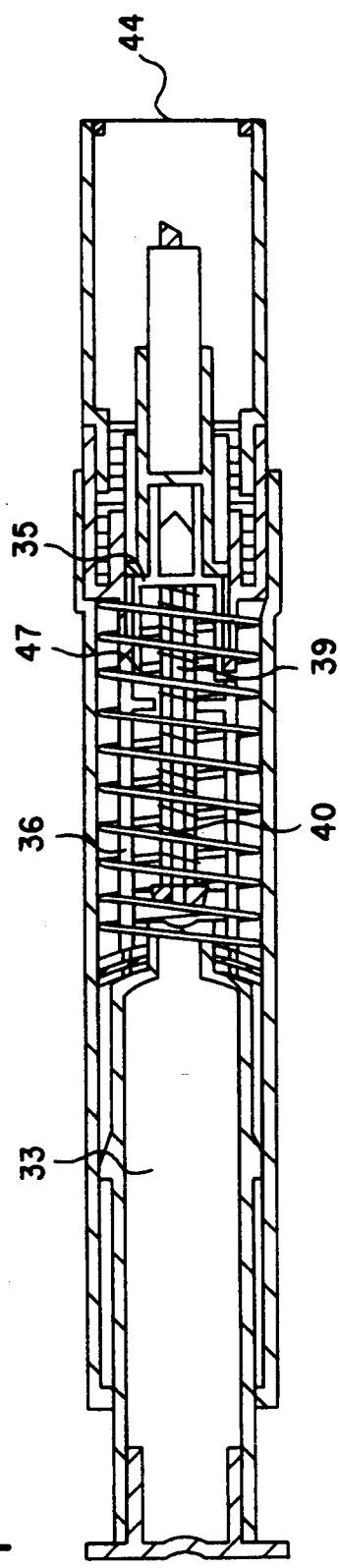
Figure 15:
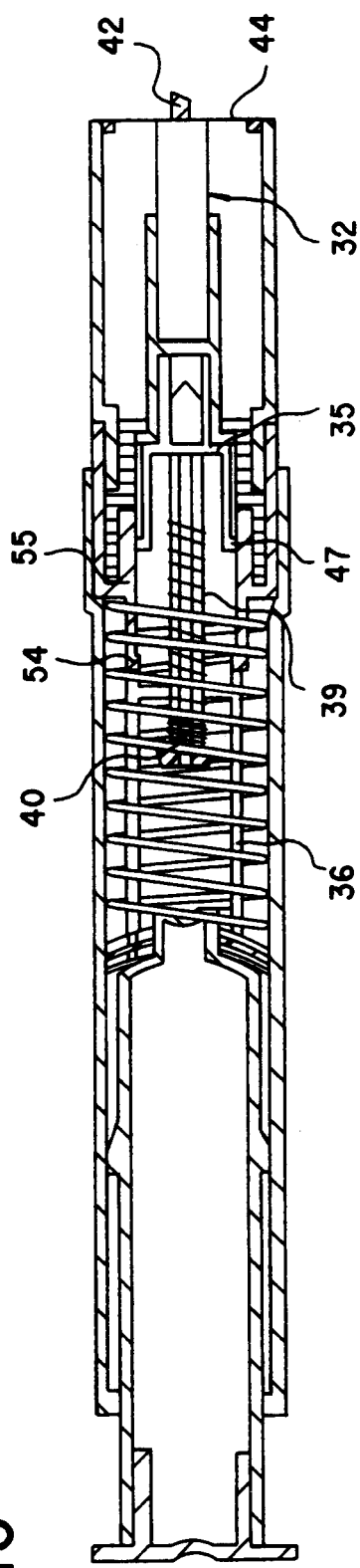
Figure 16:
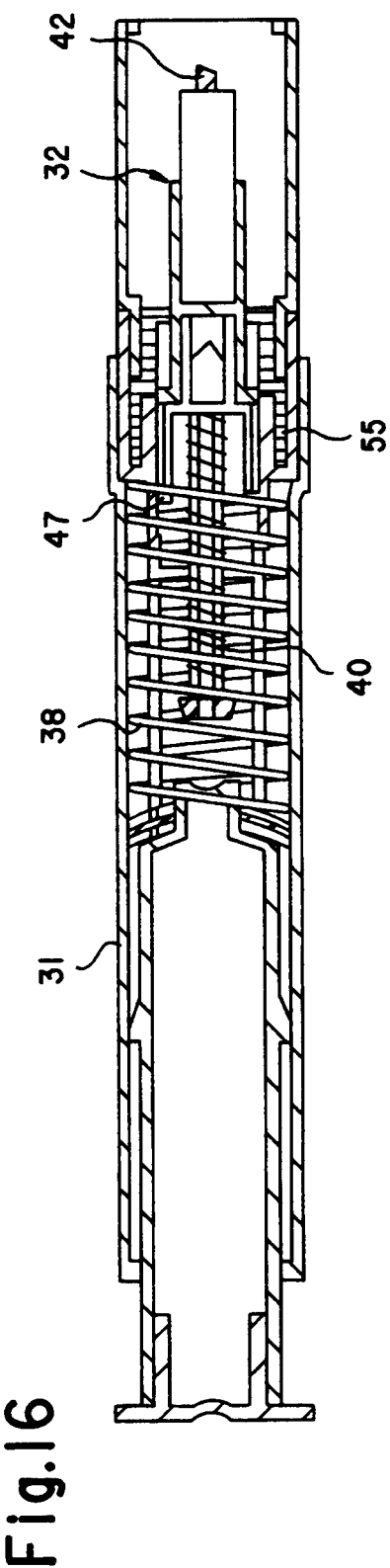

The plunger 33 shown in FIG. 14 will be pressed further at the next step to force the front end of the cylindrical member 36 to abut against the rearward rim 54 of the second stopper 55. The detent 47 on the hookable member 35 will thus disengage from the rim 54, to thereby slidably move further into the second stopper 55. Thus, the compressed third spring 39 will cause the lancet unit 32 to spring forward. The needle 42 on the unit will protrude from the open end 44 and instantaneously penetrate the human skin, as seen in FIG. 15. Simultaneously with these movements of the members, the second spring 40 which has stretched itself in the rear region of the cylindrical member 36 will be compressed again. This spring 40 will recover, in a recoiling manner, its uncompressed position immediately after the needle 16 penetrates the skin, so as to retract the lancet unit 32 and restore the needle 42 into the housing 31 as shown in FIG. 16. The detent 47 still slides backwards within the second stopper 55.

Figure 17:
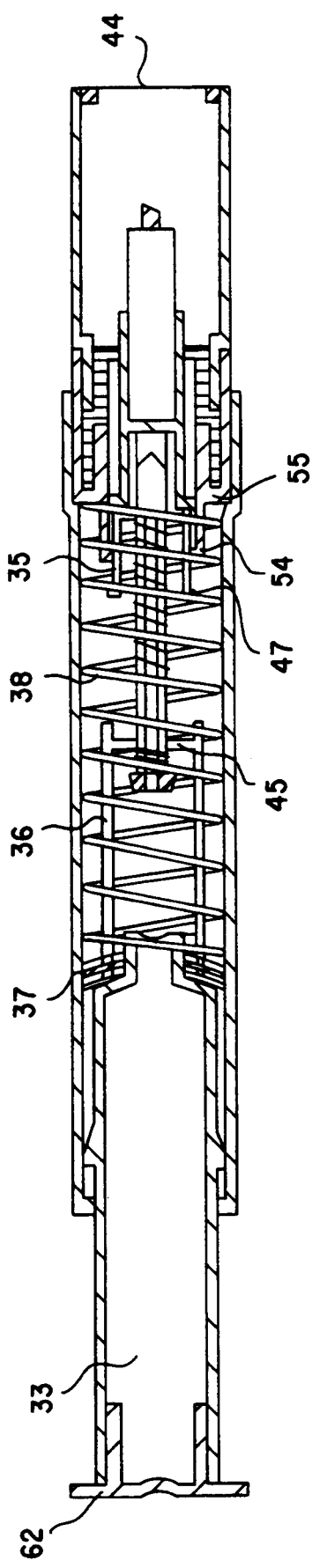

At the following final step, the plunger 33 will return to its rearward position before the open end 44 of the housing 31 is removed from the skin. This operation, which may be done manually, will however automatically take place because the first spring 38, compressed as shown in FIG. 16, will push backward the plunger 33 when an end plate 62 at the rear end of the plunger is freed from the user's hand. FIG. 17 shows such a final state of the blood sampler. The detent 47 sliding backwards within the second stopper 55 will cooperate with the cylindrical member 36 that is moving backward, to thereby allow the spring separator 45 to move the rod 34 backward. This backward movement of the rod 34 will further retract the hookable member 35 attached to the front end of the rod, beyond the rearward rim 55 and deeper into the housing 31.

The backward movement of the plunger 33 will reduce air pressure in the housing, because the gasket 37 on the front end of the plunger is in airtight contact with the inner periphery of the housing and its open end 44 is in close contact with the skin. Such a reduced air pressure enables the housing to draw or suck a sample of blood from the portion of the skin pierced by the needle.

The user may press the plunger 33 when the quantity of the sample blood is sufficient for blood tests. As the plunger advances forward a little, a gap will appear between the periphery of the gasket 37 and the inner periphery of the housing 31. Ambient air will flow into the housing to recover the atmospheric pressure therein so that no additional blood will be taken. The recovered air pressure will make it possible to remove the open end 44 of the housing 31 away from the skin with which it has been in close contact. The removal of the open end is easy and smooth and prevents any amount of blood from spilling or scattering. In FIGS. 17 and 18, the user pushes the plunger 33 a distance to recover atmospheric pressure in the housing. Small apertures may be formed, instead, through the tip 58 and the end plate 62 for that purpose. In this case, the user will close with his or her fingers the aperture in the end plate to maintain the reduced pressure in the housing 31, during the blood sampling. Upon completion of the sampling, he or she will open the aperture to introduce into the housing ambient air to recover the atmospheric pressure.

In summary, the suction-type blood sampler provided in the invention has a needle which can quickly pierce the human skin. Therefore, no sharp pain will be felt by people from whom the blood samples are taken. The blood sampling is now possible even if the density of fine blood vessels is low in the skin portion, because the blood emerging from the skin portion is sucked or drawn by a vacuum. By introducing ambient air into the housing to compensate the evacuation thereof, a required amount of blood can be taken accurately and without any fear that the blood scatters or flows away when the open end of the housing is removed from the skin.

What is claimed is:

1. A suction-type blood sampler comprising:
   a housing;
   a lancet unit positioned in a front region of the housing;
   a rod connected to and extending in a direction away from the lancet unit;
   a plunger provided in a rear region of the housing and having a gasket attached to a forward end of the plunger;
   said rod connected to said plunger;
   said housing having an open frontal end and an open rearward end;
   said lancet unit including a lancet body fixed to a lancet retainer, said lancet body having a needle extending forwardly therefrom;
   said lancet retainer being in sliding contact with an inner peripheral surface of said housing;
   a first spring and a second spring provided in the housing between the lancet unit and the plunger and a third spring within said plunger, wherein said first spring urges said lancet unit forward to move said needle outwardly of said housing, and said second spring urges said lancet unit to be retracted behind said frontal end, and wherein said third spring controls reduction of air pressure in said housing, in response to movement of said plunger.

2. A suction-type blood sampler as defined in claim 1, further comprising a protrusion integral with an intermediate portion of said rod and a concave detent formed in and integral with said housing, said concave detent separates said first spring from said third spring and is engageable with said protrusion, said plunger having an axial bore in which a flange, attached to a rear end of said rod is slidably accommodated so that said second spring is positioned between said flange and a front end of said axial bore.

3. A suction-type blood sampler as defined in claim 1, wherein said first spring is positioned between said lancet unit and said gasket, and further comprising a flange, an inner cylindrical member, a hookable member and a spring separator, wherein said separator is positioned around said rod and integral with said inner cylindrical member which extends forwardly from said plunger, said third spring positioned between lancet unit and said separator, with said second spring being interposed between said separator and said flange, and wherein said hookable member is received in a rear recess of said lancet unit and engageable with a rearward rim extending from said inner periphery of said housing.

4. A suction-type blood sampler as defined in claim 1, further comprising a cap attached to said frontal end of said housing, and at least one lug formed in and integral with an inner periphery of said cap, said lug being behind a frontal end thereof so as to delimit forward movement of said lancet unit.

5. A suction-type blood sampler as defined in claim 1, further comprising at least one lug formed in and integral with said inner periphery of said housing, said lug being behind a frontal end thereof so as to delimit forward movement of the lancet unit.

6. A suction-type blood sampler as defined in claim 1, wherein the gasket comprises a front disc, a rear disc and a flexible sheet sandwiched therebetween, said gasket being in sliding contact with said inner periphery of said housing, said front disc being of a diameter smaller than said rear disc.

7. A suction-type blood sampler as defined in claim 1, further comprising a ventilation bore formed in the plunger so as to introduce ambient air into said housing.

8. A suction-type blood sampler as defined in claim 2, wherein the gasket comprises a front disc, a rear disc and a flexible sheet sandwiched therebetween, said gasket being in sliding contact with said inner periphery of said housing, said front disc being of a diameter smaller than said rear disc.

9. A suction-type blood sampler as defined in claim 3, wherein the gasket comprises a front disc, a rear disc and a flexible sheet sandwiched therebetween, said gasket being in sliding contact with said inner periphery of said housing, said front disc being of a diameter smaller than said rear disc.

10. A suction-type blood sampler as defined in claim 4, wherein the gasket comprises a front disc, a rear disc and a flexible sheet sandwiched therebetween, said gasket being in sliding contact with said inner periphery of said housing, said front disc being of a diameter smaller than said rear disc.

11. A suction-type blood sampler as defined in claim 5, wherein the gasket comprises a front disc, a rear disc and a flexible sheet sandwiched therebetween, said gasket being in sliding contact with said inner periphery of said housing, said front disc being of a diameter smaller than said rear disc.

12. A suction-type blood sampler as defined in claim 2, further comprising a ventilation bore formed in the plunger so as to introduce ambient air into said housing.

13. A suction-type blood sampler as defined in claim 3, further comprising a ventilation bore formed in the plunger so as to introduce ambient air into said housing.

14. A suction-type blood sampler as defined in claim 4, further comprising a ventilation bore formed in the plunger so as to introduce ambient air into said housing.

15. A suction-type blood sampler as defined in claim 5, further comprising a ventilation bore formed in the plunger so as to introduce ambient air into said housing.

* * * * *